(12) United States Patent
Ciobanu et al.

(10) Patent No.: US 12,195,572 B2
(45) Date of Patent: Jan. 14, 2025

(54) NON-ISOCYANATE POLYURETHANE THERMOREVERSIBLE HYDROGEL AND METHOD FOR ITS PREPARATION

(71) Applicant: INSTITUTUL DE CHIMIE MACROMOLECULARĂ PETRU PONI, Iași (RO)

(72) Inventors: Constantin Ciobanu, Iasi (RO); Mădălina-Luiza Grădinaru, Iasi (RO); Laurențiu-Daniel Tigau, Bucharest (RO)

(73) Assignee: INSTITUTUL DE CHIMIE MACROMOLECULARA PETRU PONI, Iasi (RO)

( * ) Notice: Subject to any disclaimer, the term of this patent is extended or adjusted under 35 U.S.C. 154(b) by 959 days.

(21) Appl. No.: 17/266,471

(22) PCT Filed: Apr. 14, 2019

(86) PCT No.: PCT/RO2019/000012
§ 371 (c)(1),
(2) Date: Feb. 5, 2021

(87) PCT Pub. No.: WO2020/209740
PCT Pub. Date: Oct. 15, 2020

(65) Prior Publication Data
US 2021/0301057 A1    Sep. 30, 2021

(51) Int. Cl.
*C08J 3/075* (2006.01)
*C08F 287/00* (2006.01)
*A61L 27/38* (2006.01)
*A61L 27/52* (2006.01)

(52) U.S. Cl.
CPC .............. *C08F 287/00* (2013.01); *C08J 3/075* (2013.01); *A61L 27/3808* (2013.01); *A61L 27/52* (2013.01); *C08J 2351/08* (2013.01)

(58) Field of Classification Search
CPC ...... A61L 27/3808; C08J 3/075; C08F 287/00
See application file for complete search history.

(56) References Cited

U.S. PATENT DOCUMENTS

2004/0091982 A1    5/2004    Gee et al.
2015/0335749 A1   11/2015   Schieker et al.

FOREIGN PATENT DOCUMENTS

CN      103865059   *   6/2014   .......... C08G 63/685
WO    2011109732 A2    9/2011

OTHER PUBLICATIONS

Gradinaru et al. synthesis and rheology of thermoreversible polyurethane hydrogels, Cent. Eur. J. Chem 10(6) 1859, 2012 (Year: 2012).*
Y. Zhang et al. polyethylene glycol, comprehensive Biotechnology 5.09.2.5, 2011 (Year: 2011).*
CN103865059 English Translation (Year: 2014).*
Written Opinion and International Search Report of PCT/RO2019/000012; mailed Jan. 1, 2020.

* cited by examiner

*Primary Examiner* — Catherine S Branch
*Assistant Examiner* — Huihong Qiao
(74) *Attorney, Agent, or Firm* — Polsinelli PC

(57) ABSTRACT

The present invention relates to non-isocyanate polyurethane thermoreversible hydrogel comprising poloxamers, aliphatic di-urethanes, aliphatic di-esters and polyethylene glycol and to a method for their preparation.

17 Claims, 2 Drawing Sheets

Figure 1:
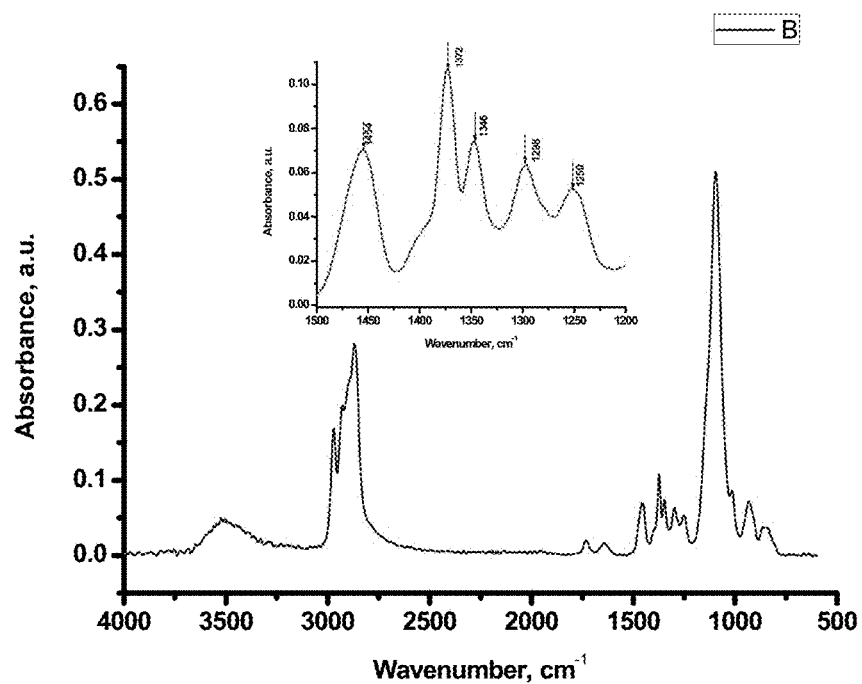

NON-ISOCYANATE POLYURETHANE THERMOREVERSIBLE HYDROGEL AND METHOD FOR ITS PREPARATION

CROSS-REFERENCE TO RELATED APPLICATIONS

The present application is a national stage entry of PCT/RO2019/000012 and hereby expressly incorporates by reference said application in its entirety.

The present invention relates to new non-isocyanate polyurethane thermoreversible hydrogels for use in the bio-medical and pharmaceutical fields and to methods for their preparation.

STATE OF THE ART

Thermoreversible hydrogels are known to be used in the bio-medical filed, for instance by performing minimally invasive interventions wherein such hydrogels are injected in liquid state into living tissues, where they convert at body temperature to a gel state, useful for tissue engineering or for the local and/or controlled delivery of pharmaceuticals, cells, proteins, etc.

US 20150335749 discloses the use of chain-extended poloxamers as thermoreversible hydrogels. Poloxamers are polyoxyethylene-polyoxypropylene-block copolymers, such as (poly(ethylene oxide)-poly(propylene oxide)-poly(ethylene oxide) (PEO-PPO-PEO) triblock copolymers known under the trade name "Pluronic", which organize into hydrophilic outer blocks and hydrophobic inner blocks. The PPO group has the characteristic that it is hydrophobic at temperatures over 288K (about 15° C.) and water soluble at temperatures under 288K. The triblock copolymer PEO-PPO-PEO forms a three-dimensional mycelium at temperatures over 288K and organizes into a hydrophobic core that contains the PPO blocks associated with one another, and a hydrophilic corona that consists of the PEO blocks that dissolve in water. Thus, when warming up to the body temperature, these hydrogels turn from liquid state into gel state (mycelium), which allows for their filling up a desired space and maintaining their shape and position. However, such poloxamer hydrogels have poor mechanical characteristics, showing low mechanical strength and swelling capacity, and a poor stability in gel form.

WO 2014/016857 discloses heat-sensitive sol-gel compositions which are thermoreversible hydrogels capable of being injected, composed of at least an amphiphilic polyurethane synthesized in a polymerization reaction between polyol containing polyethylene glycol and at least one isocyanate. Such isocyanate-containing polyurethanes have improved mechanical properties as compared to the previously used poloxamers. However, the use of isocyanates has important drawbacks, as they are known to be harmful for human health and are also very expensive substances.

Technical Problem

The present invention is directed to providing new high-quality non-isocyanate polyurethane thermoreversible hydrogel structures with good mechanical properties that have low toxicity and low preparation costs, and are easily biodegradable into compounds naturally occurring and bioactive (useful in the living organisms). Also, the present invention is directed to providing a method for the controlled preparation of hydrogel structures having specific desired properties, using low-cost, renewable and biodegradable materials.

The Hydrogel

It represents one aspect of the present invention new non-isocyanate polyurethane thermoreversible hydrogel structures able to solve the technical problem mentioned above, having the general formula I:

$$HO-\{M-Y\}_n-A-H \qquad \text{Formula I}$$

wherein:

HO— represents a hydroxyl group;

M represents a moiety which is represented by a moiety X or moiety Z, such that at least one X moiety and at least one Z moiety are present in the formula I, wherein:

each moiety X represents one of the poloxamers with the formula:

$$-(CH_2-CH_2-O)_a-(CH_2-CH(CH_3)-O)_b-(CH_2-CH_2-O)_a-$$

wherein a is an integer from 20 to 100 and b is an integer from 70 to 85;

each moiety Z represents one of the aliphatic di-urethanes with the formula:

$$-R_1-OOCNH-R_2-NHCOO-R_1-,$$

wherein $R_1$ represents an aliphatic radical with 2 to 3 carbon atoms and $R_2$ represents an aliphatic moiety with 2 to 8 carbon atoms, preferably 3 to 6 carbon atoms;

each Y represents one of the aliphatic diester moieties with the formula:

$$-OOC-(CH_2)_y-COO-,$$

wherein y represents an integer between 2 and 10, preferably between 2 and 8;

A represents a PEG (polyethylene glycol) moiety having the formula:

$$-(CH_2-CH_2-O)_w-$$

with a molecular mass of 400 to 3000 g/mole, preferably 1000 to 2500 g/mole, most preferably about 2000 g/mole, wherein w is an integer representing the number of ethylene glycol moieties in the PEG;

n represents the degree of polymerization and is an integer from 2 to 12, preferably from 2 to 6.

Hydrogel Detailed

In the disclosed formula I, the moiety X is a poloxamer with the formula -$PEO_a$-$PPO_b$-$PEO_a$- [-(polyethylene oxide)$_a$-(polypropylene oxide)$_b$-(polyethylene oxide)$_a$-], wherein a is an integer from 20 to 100 and b is an integer from 70 to 85. Such poloxamers are also known under the trademark name Pluronic. In the same hydrogel molecule of formula I, different moieties X may represent different poloxamers.

In preferred embodiments, moiety X is chosen from Pluronic P-123, which is a poloxamer having a molecular mass of 5800 g/mole and wherein a=20 and b=70, and/or Pluronic F-127, which is a poloxamer having a molecular mass of 12600 g/mole and wherein a=100 and b=83. Of the two mentioned poloxamers, Pluronic P-123 is preferred, because it can react with several hard urethane segments and the resulted gel is better structured.

In an alternative embodiment, the different moieties X of the hydrogel of formula I may represent Pluronic P-123, Pluronic F-127, and PEG with a molecular mass of 400 to 3000 g/mole, preferably 1000 to 2500 g/mole, most preferably about 2000 g/mole.

In the disclosed formula I, Y represents an aliphatic diester moiety with the formula: —OOC—$(CH_2)_y$—COO—, wherein y represents an integer between 2 and 10, preferably between 2 and 8. In the same hydrogel molecule of formula I, different moieties Y may represent different aliphatic diesters.

Aliphatic diesters Y mentioned above have hydrophobic effect, given by their aliphatic moiety, which forms hydrophobic interactions intra- and inter-molecularly with other aliphatic moieties in the polymeric chain. By choosing the number of —$CH_2$— groups (from 2 to 10, preferably from 2 to 8) of the aliphatic diester(s) used, it is possible to directly and finely adjust the hydrophobic interactions in the hydrogel molecule, thus efficiently controlling the gel point (the temperature where the transition from solution to gel takes place) and the stability of the gel at body temperature. Such an easy and fine adjustment was not previously possible for hydrogels with only components with high molecular masses, such as Pluronic.

In preferred embodiments, the moiety Y is represented by the aliphatic diesters of succinic acid (y=2), glutaric acid (y=3) and/or sebacic acid (y=8). Such diesters can be obtained efficiently, ecologically and in low cost processes from renewable materials. For instance, succinic acid can be obtained by fermenting glucose with *Actinobacillus succinogenes*, the butyric acid can be obtained by fermenting the molasses using *Clostridium tyrobutyricum*, and sebacic acid can be obtained by caustic oxidation of castor oil. Such fermentation processes have a substantially lower cost than processes starting from petroleum. Also, these substances have the further advantage of being very desirable biodegradation products. Succinic acid is the precursor for succinate dehydrogenase (SDH), which plays an important role in mitochondrial function, being both part of the respiratory chain and the Krebs cycle. Butyric acid is considered the main energy substrate for colonocytes and a factor that stimulates their growth and differentiation. From sebacic acid very good biomaterials are obtained such as poly (glycerol-co-sebacate).

In the disclosed formula I, moiety Z represents at least one of the aliphatic di-urethanes with the formula: —$R_1$—OOCNH—$R_2$—NHCOO—$R_1$—, wherein $R_1$ represents an aliphatic radical with 2 to 3 carbon atoms and $R_2$ represents an aliphatic moiety with 2 to 8 carbon atoms, preferably 3 to 6 carbon atoms. In the same hydrogel molecule of formula I, different moieties Z may represent different aliphatic di-urethanes.

Thus, moiety Z of the disclosed formula I is represented by at least a hard di-urethane, which is able to form hydrogen bonds in the polymeric chain, intra-molecularly and inter-molecularly with other aliphatic di-urethane molecules and with diesters Y. The introduction of a di-urethane moiety in the polymeric chain confers the hydrogel improved rheological properties (as illustrated by the elastic modulus G' and loss modulus G"), ensuring that the gel state (the mycelium, the crystalline form) remains stable in the temperature interval between 21.3 and 49.4° C. and has an elasticity module comparable to that of the tissue extracellular matrix. Also, di-urethane Z is advantageously biodegradable and bioactive, allowing cells to adhere to it and to grow. In the preferred process for preparation of the hydrogel, the aliphatic di-urethane Z is prepared without isocyanates or catalysts, by the reaction of a diamine with a carbonate, preferably an ethylene or propylene carbonate.

Radical $R_1$ of moiety Z has 2 or 3 carbon atoms. Such aliphatic di-urethanes Z can be prepared by the polyaddition reaction between ethylene or propylene carbonate with a diamine. Both ethylene carbonate and propylene carbonate can be prepared using available, abundant, economic and renewable sources of carbon, such as $CO_2$, and are biodegradable substances with low toxicity. Such a structure of moiety Z wherein radical $R_1$ has 2 or 3 carbon atoms is particularly useful for preparing thermoreversible hydrogels suitable for minimally invasive surgery in general and particularly for hydrogels having high affinity for endothelial and progenitor heart cells for the treatment of heart attacks.

In preferred embodiments, moiety Z is represented by a di-urethane wherein radical $R_2$ has 4 or 5 carbon atoms. As a consequence, the hydrogel of the invention biodegrades within the living organism into the biogenic diamines 1,4-butanediamine (tetramethylenediamine or putrescine), or 1,5-pentanediamine (pentamethylenediamine or cadaverine). Such biogenic diamines are compounds with low molecular mass normally occurring in living organisms from the decomposition of amino acids. Tetramethylenediamine and pentamethylenediamine have important physiological functions in the development and survival of cells, such as serving as nitrogen sources and precursors for the production of hormones, alkaloids, nucleic acids, etc. Also, it is advantageous to use in the process of production of the hydrogel such biogenic diamines, which can be obtained by a non-toxic, low cost process of biosynthesis from renewable materials by biotechnological fermentation. For instance, putrescine can be produced by hydrogenation of succinonitrile and cadaverine is obtained by decarboxylation of lysine in alkaline medium.

Moiety A of the disclosed formula I represents a PEG (polyethylene glycol) moiety having the formula: —$(CH_2$—$CH_2$—$O)_w$—, with a molecular mass of 400 to 3000 g/mole, preferably 1000 to 2500 g/mole, most preferably about 2000 g/mole, wherein w is an integer representing the number of ethylene glycol moieties in the PEG. The molecular mass of the PEG used can chosen from the range molecular mass of 400 to 3000 g/mole, preferably 1000 to 2500 g/mole, most preferably about 2000 g/mole; the corresponding degree of polymerization w of the PEG can be thus computed. Moiety A has hydrophilic ether groups and also the hydrophilic terminal hydroxyl group. Thus, together with the hydrophobic ester group of adjacent aliphatic diester Y, a hydroxyl-ether-ester structure is formed at the end of the polymeric chain which confers a further amphiphilic effect to the hydrogel of the invention.

Advantages

The particular combinations of moieties in the hydrogels of the invention ensure that they are especially suited for different bio-medical applications. The particular chemical structure of the hydrogel ensures that it is particularly suited for drug delivery, and also that it easily biodegrades in the living organism: carboxylesterases from the body catalyze the hydrolysis of the ester and urethane groups into soluble acids and amines, respectively. The micelles formed by the hydrocels of the invention are stable in a large temperature range, from 21.3° C. until 49.4° C. Moreover, by choosing appropriate moieties in formula I of the invention, and by modifying the degree of polymerization n, we can obtain hydrogels with different properties, as needed for different applications thereof, such as water solubility, viscosity, elasticity, LCST (lower critical solution temperature), and UCST (upper critical solution temperature). For instance, for injectable hydrogels a low viscosity is required, so for this application a hydrogel of the invention will have a degree of polymerization n between 1 to 4, preferably 1 or 2. Also, as mentioned before, by choosing an aliphatic diester Y with a certain number of —CH2- groups (from 2 to 10), it is possible to directly and finely adjust the hydrophobic effect in the hydrogel molecule, thus efficiently controlling the gel point (the temperature where the transition from solution to gel takes place) and the stability of the gel at body temperature.

In aqueous gel solution, the hydrogel of the invention easily dissolves bovine serum albumin (BSA), human serum albumin (HSA), tripeptide Arg-Gly-Asp (RGD), Hepatocyte Human Bone Morphogenetic Protein 4 (BMP-4) human, Growth Factor HGF human, elastin, soluble collagen, which aids the adhesion and proliferation of progenitor cells and endothelial cells.

Properties. Determination

The various properties of the hydrogels of the invention have been assessed as follows. The structural determination of the hydrogels according to the invention was performed at 25° C. by Fourier-transform infrared spectroscopy (FTIR) with a Bruker Vertex 70 spectrometer equipped with an ATR diamond device (Golden Gate, Bruker) and with software for spectral processing.

The number average molar mass (Mn), the mass average molar mass (Mw), as well as the molar mass distribution (molecular weight distribution) Mw/Mn of the hydrogel of the invention have been determined by gel permeation chromatography (GPC) at 25° C. using a GPC PL-EMD 950 equipped with evaporation molecular weight detector. For applications of the hydrogel of the invention suitable for injection, the number average molecular mass (Mn), which directly influences the rheology of the hydrogel can vary between about 14000-17000 Da, and the molar mass distribution varies between about 1.3 and 1.6.

Glass transition temperature (Tg) behavior of hydrogel samples prepared by drying at temperature 50° C. and low pressure, 01-02 mmHg, was measured by Differential scanning calorimetry (DSC). Measurements were performed by means of a Pyris Diamond (Perkin Elmer) instrument. The samples, having a mass of 6-8 mg, were placed into aluminum foil pans. DSC curves were recorded in nitrogen atmosphere (20 mL min-1 flow) with a heating rate of 5° C. min-1 for a temperature range from −100 to −40° C. Glass transition temperature was taken as the inflexion point of the DSC curve. Two runs were performed for each sample. High purity (98%) indium with melting temperature at 156.68° C. and melting enthalpy of 28.4 J g$^{-1}$ was used as a reference.

It was thus found that the glass transition temperature of hydrogels, according to the invention, characterizes the range −62° and −53° C.

The rheological properties of the hydrogel were determined with a Bohlin CVO rheometer, using plates will parallel geometry (wherein the plate has a superior radius of 30 mm, and the gap between the plates is of 500 am), equipped with a Peltier temperature controller, wherein the prevention of water evaporation was made with an anti-evaporation device.

The elastic moduli of the hydrogel, namely the elastic modulus G' (elastic energy of the accumulated tension) and loss modulus G" (elastic energy of the lost energy) were determined. The value of G' raises with the number and strength of the hydrophobic interactions and hydrogen bonds in the hydrogel molecules. The value of G" describes the energy dissipated or lost in a sinusoidal cycle of tension per unit of volume and represents the viscous component. The ratio G"/G'=tan δ illustrates the behavior of the hydrogel: when tan δ is high (G" greater than G'), the hydrogel has a viscous behavior, and when tan δ is low (G' greater than G") the hydrogel has an elastic behavior. Thus, it was determined that the hydrogel of the invention makes the transition from solution to gel in a very short time: in a preferred embodiment, the complex viscosity reaches maximum value within 44 seconds. Moreover, G' and G" of the hydrogel of the invention were found to remain constant over a large temperature range (from about 21.3° C. to about 49.4° C.), which shows that the molecule of hydrogel becomes very well-structured into a three-dimensional network by forming hydrogen bonds, hydrophobic interactions, van der Waals forces and by entanglement.

The point of intersection between G' and G" represents the lower critical solution temperature (LCST), which is the lowest temperature where the solution turns into gel. Advantageously, the hydrogel of the present invention typically has a LCST value of about 21.3° C., which low value makes it very suitable for fast gel structuring at body temperature.

Method of Preparation

It represents a further object of the present invention a method for the preparation of a high-quality non-isocyanate polyurethane thermoreversible hydrogel of formula I, comprising the following steps:
  i) ethylene carbonate and/or propylene carbonate is dissolved in pure water without $CO_2$ in a suitable reactor;
  ii) an aqueous solution of an aliphatic diamine with 2 to 8, preferably 2 to 6 carbon atoms is added at a temperature of 1° C. to 30° C., preferably 1 to 10° C., most preferably of about 2 to 4° C., and under inert atmosphere;
  iii) a poloxamer X as defined above is added and the composition is stirred until the pH drops under 8;
  iv) the water is eliminated from the reactor at low temperature (−100° C. to −80° C.) and low pressure (0.1-0.2 mmHg);
  v) the temperature of the anhydrous paste obtained after step iv) is slowly raised to about 20° C. to 100° C., preferably 30° C. to 60° C.;
  vi) an aliphatic diester Y as defined above is added under energetic stirring and the resulting gases are eliminated, for example with a vacuum pump;
  vii) PEG is added and the system is homogenized, and the resulting gases are eliminated, for example with a vacuum pump.

Method Detailed

The method of the invention allows for the macromolecular chain to grow in controlled steps by polyaddition and polycondensation reactions between the reactants, without using any toxic products such as catalysts and without the use of isocyanates. This is a clean, environmentally friendly method using low-cost, biodegradable materials from renewable sources. All the products that result from cleaning the reactor are biodegradable.

The method has the advantage that it makes it possible to design both the molecular mass of the polymer and also its structure.

Preferably, in step i) of the method of the invention ethylene carbonate and/or propylene carbonate of 99% purity is mixed with pure water without $CO_2$ in a suitable reactor at room temperature (15 to 25° C.) or higher, preferably at about 35° C., under light stirring, until solved. A suitable reactor may advantageously be a reactor provided with stirring means, a vacuum pump and a nitrogen line.

Preferably, in step ii) of the method of the invention, because the polyaddition reaction of the carbonate with the diamine is exothermic, the temperature of the solution obtained in step i) is first lowered to about 1 to 30° C., preferably 1 to 10° C., most preferably to about 2 to 4° C., and then an aqueous solution in pure water without $CO_2$ of at least an aliphatic diamine with 2 to 8, preferably 2 to 6, carbon atoms, is added, drop by drop and under light mixing. The diamine solution is advantageously added under a pure $N_2$ blanket, thus ensuring that no reaction with the atmospheric $CO_2$ occurs.

Then, in step iii) of the method of the invention, a poloxamer HO—X—OH, wherein X is as defined above, is added. The resulting composition is left until its pH drops under 8; basically the pH drops under 8 when all the diamine has been consumed in the polyaddition reaction of the diamine(s) with the carbonate(s) to form an aliphatic dihydroxy di-urethane HO—Z—OH. An example of the corresponding reaction is given below:

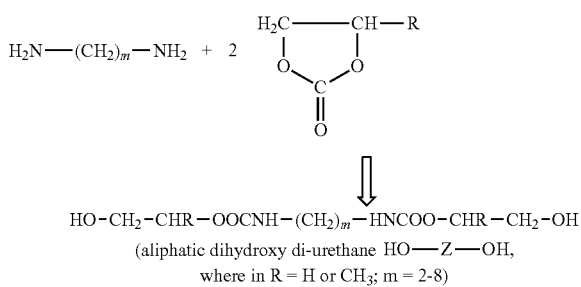

(aliphatic dihydroxy di-urethane HO—Z—OH,
where in R = H or $CH_3$; m = 2-8)

Preferably, in step iv) of the method of the invention the water is eliminated from the system (reactor) rapidly and efficiently by using a vacuum pump and a rotary evaporator at low temperature (−100° C. to −80° C.) and low pressure (0.1-0.2 mmHg), thus resulting an anhydrous paste. It is important to efficiently eliminate the water from the system, because it would otherwise form hydrates with the final compound, which would be then very difficult to decompose.

In step v) of the method of the invention the temperature of the anhydrous paste obtained in step iv) is slowly raised to about 20 to 100° C., preferably 30 to 60° C., most preferably about 53° C., and the system is homogenized.

In step vi) of the method of the invention the aliphatic diester(s) R—Y—R, wherein Y is as defined above and R is an aliphatic radical, preferably a methyl, is/are added under energetic stirring. The polycondensation reaction takes place, and the resulting gases (e.g. methyl alcohol) are eliminated, for example with a vacuum pump. By measuring the quantity of the collected gases (i.e. methyl alcohol) we can monitor the desired degree of polycondensation.

After the desired degree of polycondensation n has been obtained, PEG is added and the polycondensation reaction is stopped, thereafter the system is homogenized, and the resulting gases are eliminated, for example with a vacuum pump, resulting the final hydrogel.

An example of the chain of reactions in steps vi)-vii) is given below:

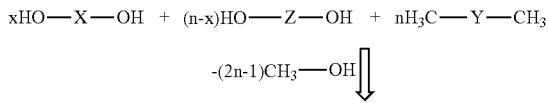

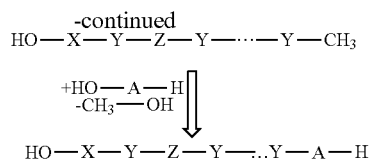

There are further given, without limiting generality, some embodiments in connection also with the figures, which represent:

FIGURES

FIG. 1—Illustrates the characteristic vibrations FTIR for a hydrogel according to example 1 of the invention measured at 25° C.

Figure 2:
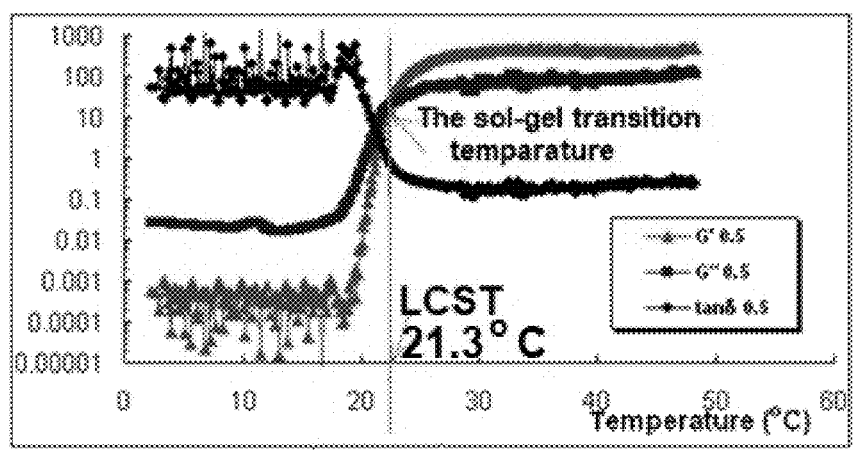

FIG. 2—illustrates, for example 1 of the invention, the evolution with temperature of viscoelastic parameters (G', G", tan δ) at a heating rate of 0.5° C./min (1 Pa, 1 rad/s)

Figure 3:
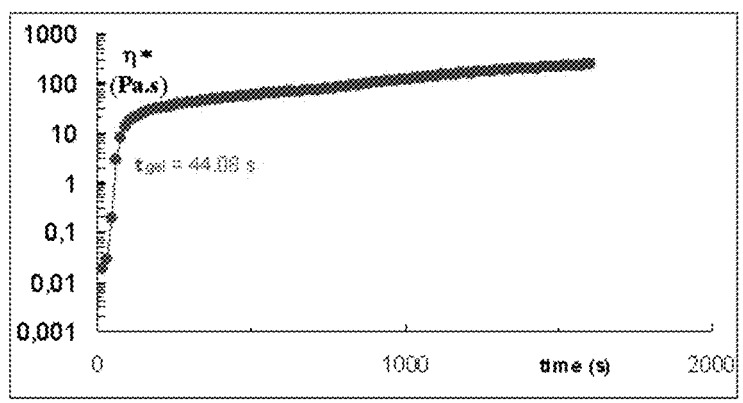

FIG. 3—illustrates, for Example 1 of the invention, the evolution of complex viscosity (η*) as a function of time (t) at 37° C., during gelation.

EXAMPLE 1

1.0566 g (0.0012 moles) of etylene carbonate 99% (Sigma-Aldrich) were placed in a 250 $cm^3$ cylindric glass reactor equipped with stirring means, vacuum pump and a nitrogen supply. 2 ml pure water without $CO_2$ were then added and gently stirred for 20 minutes at 35° C. The temperature was then lowered to 2-4° C. and then, under pure $N_2$ blanket and energetic stirring, a solution of 0.6 ml (0.006 moles) of 1,4-butanediamine (putrescene) 99% (Sigma Aldrich) in 2 ml pure water without $CO_2$ was added drop by drop over 60 minutes. Thereafter, the components were lightly stirred together for another 4 hours, and then 116 g of Pluronic P-123 (Sigma-Aldrich) were added and the light stirring is continued for another 20 hours. The reactor was then coupled to the vacuum pump provided with a trap for retaining water at −100 to −80° C. and low pressure (0.1 to 0.2 mmHg), and the water was eliminated from the system for 8 hours, resulting an anhydrous paste having pH 7.4 to 7.6 at 25° C. The temperature of the system was slowly raised to 53° C., under dry nitrogen blanket, and then 8.3 g of dimethyl sebacate 99% (Sigma-Aldrich) were added under energetic stirring, after which the vacuum pump was turned on for 4 hours. Then, 40 g polyethylene glycol (PEG BioUltra 2000 (Sigma-Aldrich)) were added and the system was homogenized and the resulting gases were pumped out until eliminated. At the end of this process, it is obtained a thermoreversible polyurethane hydrogels soluble in water or normal saline with the general formula:

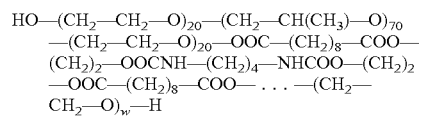

The properties of the hydrogel thus obtained are depicted in FIGS. 1 to 3.

In FIG. 1, are illustrated the characteristic vibrations FTIR for the hydrogel of example 1, measured at 25° C. by Fourier-transform infrared spectroscopy (FTIR) with a Bruker Vertex 70 spectrometer equipped with an ATR diamond device (Golden Gate, Bruker) and with software for spectral processing.

The asymmetric vibrations ν(CH)$_{asym}$ from the CH$_3$ and CH$_2$ groups are those at 2966 and 2921 cm$^{-1}$, and the symmetrical vibrations of the same groups are those at 2902 and 1866 cm$^{-1}$. At the 1732 cm$^{-1}$ appear the vibration of the urethane carbonyl group and the ester ν (C=O). Carbonyl vibration occurs so far because their concentration in the polymer matrix is small and they can no longer form urethane-urethane hydrogen or urethane ester bonds. At 1642 cm$^{-1}$ vibrates the δ (H—O) linkage in water and at 1566 and 1552 cm$^{-1}$ we have the specific vibrations from amide II (ν (C—N)+δ (N—H)). At 1454 cm$^{-1}$ there is the asymmetrical deformation vibration δ (C—H)$_{asym}$ from the CH$_3$ group, and symmetrical vibration δ (C—H)$_{sym}$ is at 1346 cm$^{-1}$. The vibrations of amide III (ν (C—N)+δ (N—H)) are found at 1250 cm$^{-1}$ and at 1115 cm$^{-1}$ there are ν C—O$_{sym}$ of CH$_2$—O—CH$_2$ and CH$_2$—O—HC(CH$_3$).

In FIG. 2 is illustrated the evolution with temperature of viscoelastic parameters (G', G", tan δ) of the hydrogel of example 1 at a heating rate of 0.5° C./min (1 Pa, 1 rad/s), and in FIG. 3 is illustrated the evolution of complex viscosity (η*) of the hydrogel of example 1 as a function of time (t) at 37° C., during gelation.

EXAMPLE 2

The process was carried out as in example 1, with the difference that, instead of 1,4-butanediamine was used 1,5-pentanediamine (cadaverine) in a concentration of at least 97% (Sigma Aldrich), and instead of ethylene carbonate 99% (Sigma-Aldrich) was used propylene carbonate 99.7% (Sigma-Aldrich).

EXAMPLE 3

The process was carried out as in example 1, with the difference that, instead of Pluronic P-123 100% was used a mixture of 12.6 g Pluronic F-127 (Sigma Aldrich), 100 g Pluronic P-123 and 40.2 g PEG.

EXAMPLE 4

The process was carried out as in example 1, with the difference that, instead of dimethyl sebacate it is used a mixture of 6 g dimethyl sebacate, 0.8 g dimethyl glutarate at least 98% (Sigma Aldrich) and 0.73 g dimethyl succinate 98% (Sigma Aldrich).

The properties of the hydrogels of Examples 1-4 above are depicted in the following Table 1, wherein:
HC=Hydrogel concentration
Mn=number average molar mass;
Mw=mass average molar mass;
Mw/Mn—molar mass distribution;
Tg—glass transition temperature;
GT—gelling time at 37° C. deduced from complex viscosity (η*).

| Example, No | HC, % | Mn, Da | Mw, Da | Mw/Mn | Tg, ° C. | GT second |
|---|---|---|---|---|---|---|
| 1 | 12.5 | 16800 | 25704 | 1.53 | −57.52 | 44 |
| 2 | 12.5 | 17900 | 39380 | 2.20 | −62.70 | 150 |
| 3 | 12.5 | 17850 | 40341 | 2.26 | −56.72 | 108 |
| 4 | 12.5 | 16920 | 27241 | 1.61 | −55.82 | 143 |

The invention claimed is:

1. Thermoreversible hydrogel of general formula I:

HO-{M-Y}$_n$-A-H        Formula I wherein:
HO— represents a hydroxyl group;
M represents a moiety which is represented by a moiety X or moiety Z, such that at least one X moiety and at least one Z moiety are present in the formula I, wherein:
each moiety X represents one of the poloxamers with the formula:

—(CH$_2$—CH$_2$—O)$_a$—(CH$_2$—CH(CH$_3$)—O)$_b$—(CH$_2$—CH$_2$—O)$_a$— wherein a is an integer from 20 to 100 and b is an integer from 70 to 85;
each moiety Z represents one of the aliphatic di-urethanes with the formula:

—R$_1$—OOCNH—R$_2$—NHCOO—R$_1$—, wherein R$_1$ represents an aliphatic radical with 2 to 3 carbon atoms and R$_2$ represents an aliphatic moiety with 2 to 8 carbon atoms;
each Y represents one of the aliphatic diester moieties with the formula:

—OOC—(CH$_2$)$_y$—COO—, wherein y represents an integer between 2 and 10;
A represents a PEG (polyethylene glycol) moiety having the formula:

—(CH$_2$—CH$_2$—O)$_w$— with a molecular mass of 400 to 3000 g/mole wherein w is an integer representing the number of ethylene glycol moieties in the PEG;
n represents the degree of polymerization and is an integer from 2 to 12.

2. Thermoreversible hydrogel according to claim 1, which is free from isocyanate.

3. Thermoreversible hydrogel according to claim 1, wherein each moiety X is any of: Pluronic P-123, which is a poloxamer having a molecular mass of 5800 g/mole and wherein a=20 and b=70, Pluronic F-127, which is a poloxamer having a molecular mass of 12600 g/mole and wherein a=100 and b=83.

4. Thermoreversible hydrogel according to claim 1, wherein each moiety Y is represented by any of the aliphatic diesters of succinic acid, glutaric acid or sebacic acid.

5. Thermoreversible hydrogel according to claim 1, wherein each moiety Z is represented by a di-urethane wherein radical R$_2$ having 4 or 5 carbon atoms.

6. Thermoreversible hydrogel according to claim 1, wherein the R$_2$ represents an aliphatic moiety with 2 to 6 carbon atoms.

7. Thermoreversible hydrogel according to claim 1, wherein the y represents an integer between 2 and 8.

8. Thermoreversible hydrogel according to claim 1, wherein the A has a molecular mass of 400 to 3000 g/mole.

9. Thermoreversible hydrogel according to claim 1, wherein the A has a molecular mass of about 2000 g/mole.

10. Thermoreversible hydrogel according to claim 1, wherein the n is an integer from 2 to 6.

11. Method for the preparation of a thermoreversible hydrogel of formula I, comprising the following steps:
i) ethylene carbonate and/or propylene carbonate is dissolved in pure water without CO$_2$ in a suitable reactor;
ii) an aqueous solution of an aliphatic diamine with 2 to 8 carbon atoms is added at a temperature of 1° C. to 30° C. and under inert atmosphere;
iii) a poloxamer X as defined above is added and the composition is stirred until the pH drops under 8;

iv) the water is eliminated from the reactor at low temperature (−100° C. to −80° C.) and low pressure (0.1-0.2 mmHg);
v) the temperature of the anhydrous paste obtained after step iv) is slowly raised to about 20° C. to 100° C.;
vi) an aliphatic diester Y as defined above is added under energetic stirring and the resulting gases are eliminated;
vii) PEG is added and the system is homogenized, and the resulting gases are eliminated.

12. Method according to claim 11, wherein no isocyanates and no catalysts are used.

13. Method according to claim 11, wherein the aqueous solution of aliphatic diamine has 2 to 6 carbon atoms.

14. Method according to claim 11, wherein the aqueous solution is added at a temperature of 1° C. to 10° C.

15. Method according to claim 11, wherein the aqueous solution is added at a temperature of 2° C. to 4° C.

16. Method according to claim 11, wherein the temperature of the anhydrous paste obtained after step iv) is slowly raised to 30° C. to 60° C.

17. Method according to claim 11, wherein the temperature of the anhydrous paste obtained after step iv) is slowly raised to about 53° C.

* * * * *